United States Patent
Klimant et al.

[11] Patent Number: 6,139,798
[45] Date of Patent: *Oct. 31, 2000

[54] SENSOR MEMBRANE OF AN OPTICAL SENSOR

[75] Inventors: Ingo Klimant; Hellfried Karpf; Otto S. Wolfbeis, all of Graz, Austria

[73] Assignee: AVL Medical Instruments AG, Switzerland

[*] Notice: This patent issued on a continued prosecution application filed under 37 CFR 1.53(d), and is subject to the twenty year patent term provisions of 35 U.S.C. 154(a)(2).

[21] Appl. No.: 08/843,296

[22] Filed: Apr. 14, 1997

Related U.S. Application Data

[63] Continuation of application No. 08/709,836, Sep. 10, 1996, abandoned, which is a continuation of application No. 08/411,080, Mar. 27, 1995, abandoned, which is a continuation of application No. 08/092,993, Jul. 19, 1993, abandoned.

[30] Foreign Application Priority Data

Jul. 24, 1992 [AT] Austria ..................................... 1522/92

[51] Int. Cl.$^7$ ................................................. G01N 21/64
[52] U.S. Cl. ............................... 422/82.07; 422/82.08; 436/136; 427/163.2
[58] Field of Search .......................... 422/56, 57, 82.05, 422/82.07, 82.08, 82.11; 436/101, 122, 135, 136, 138, 139; 356/39–41; 250/458.1, 459.1; 427/163.2, 169

[56] References Cited

U.S. PATENT DOCUMENTS

| | | | |
|---|---|---|---|
| 4,752,115 | 6/1988 | Murray, Jr. et al. | 350/96.29 |
| 4,775,514 | 10/1988 | Barnikol et al. | 422/55 X |
| 4,925,268 | 5/1990 | Iyer et al. | 422/82.06 X |
| 4,994,396 | 2/1991 | Lefkowitz et al. | 436/136 |
| 5,030,420 | 7/1991 | Bacon et al. | 422/82.07 |

FOREIGN PATENT DOCUMENTS

| | | |
|---|---|---|
| 0190830 | 8/1986 | European Pat. Off. . |
| 0205232 | 12/1986 | European Pat. Off. . |

OTHER PUBLICATIONS

Neumann, G. et al. "Polyurethane Films for the Production of Membrane–covered Oxygen Sensors" Chemical Abstracts, vol. 105, No. 4, 25356v, (1986).

Wolfbeis et al., "A New Sensing Material . . . in an Aqueous Phase" in Mikrochim Acta, 1986 III, pp. 359–366.

*Primary Examiner*—Jeffrey Snay
*Attorney, Agent, or Firm*—Baker Botts LLP

[57] ABSTRACT

The sensor membrane of an optical sensor for detection of $O_2$, $H_2O_2$, $SO_2$ or halogenated hydrocarbons in a sample contains an indicator substance that is homogeneously immobilized in the polymer matrix of the sensor membrane and is, at least indirectly, in contact with the sample, changing at least one of its optical properties upon a change of the parameter to be measured. The indicator substance contains an inorganic salt of a transition metal complex with α-diimine ligands. The indicator substance is homogeneously distributed in the polymer matrix, which essentially consists of at least one substance belonging to the group of cellulose derivatives, polystyrenes, polytetrahydrofuranes, or their respective derivatives.

2 Claims, No Drawings

SENSOR MEMBRANE OF AN OPTICAL SENSOR

CROSS-REFERENCE TO RELATED APPLICATIONS

This application is a continuation of application Ser. No. 08/709,836, filed Sep. 10, 1996, now abandoned, which was a continuation of application Ser. No. 08/411,080, filed Mar. 27, 1995, now abandoned, which was a continuation of application Ser. No. 08/092,993, filed Jul. 19, 1993, now abandoned.

BACKGROUND OF THE INVENTION

The invention relates to a sensor membrane of an optical sensor for detection of $O_2$, $H_2O_2$, $SO_2$ or halogenated hydrocarbons in a sample with an indicator substance that is homogeneously immobilized in the polymer matrix of the sensor membrane and is at least indirectly, in contact with the sample, changing at least one of its optical properties upon a change of the parameter to be measured, this indicator substance containing an inorganic salt of a transition metal complex with α-diimine ligands.

DESCRIPTION OF THE PRIOR ART

There are known a large number of indicator substances and sensor membranes responding to the above mentioned substrates by a charge in one of the optical properties of the indicator. The change in this specific property, for example, fluorescence intensity, fluorescence decay time, absorption, etc., may be detected with known optical methods and apparatuses, and related to the substrate concentration to be measured.

In "A New Material for Optical Oxygen Measurement, with the Indicator Embedded in an Aqueous Phase" (Mikrochimica Acta 1986 III, 359–366), for example, indicator dyes are adsorbed on a supporting material; the supporting material doped in this manner is then embedded in a polymer matrix. As an indicator dye a ruthenium complex is used, i.e., ruthenium tris(dipyridyl)-dichloride Ru(bpy)$_3$Cl$_2$. The supporting material is silica gel, which is embedded in a silicone rubber, for instance, Silicon RTV-118 of Wacker Chemie, Burghausen, Germany. The resulting sensor membranes are characterized by high oxygen sensitivity, their signal intensity is average to low, however, and the sensor characteristic is unstable in an aqueous phase. Another disadvantage is the marked non-linearity of the technically complex and expensive sensor membrane.

Another example is given in U.S. Pat. No. 5,030,420, in which dyes, such as complexes of platinum metals with α-diimine and porphyrin ligands are used in polymers, such as PVC, plexiglass, silicone rubber, natural rubber, polycarbonate, teflon, etc. The ligands mentioned in this context include 2,2'-bipyridine (bpy), 1,10-phenanthroline (phen), and 4,7-diphenyl-1,20-phenanthroline (diph). The dye may incorporated into the polymer by diffusion, or it may be mixed with the prepolymer, or attached to the polymer by ionic or covalent bonding. This may have negative effects on essential dye characteristics, however. In particular, the immobilization of Ru(diph)-perchlorate in GE RTV SILASTIC 118 silicone rubber (General Electric, USA), which is specifically described in this patent, cannot be regarded as a proof for the solution of the dye directly in the silicone matrix, since the silicone rubber used in this case contains fillers acting as dye adsorbents, so that the dye is not dissolved in the matrix itself.

Another example is discussed in EP-A2 0 190 830, i.e., the homogeneous immobilization of transition metal complexes in polymers with high oxygen permeability, supplying the sensor membranes described above. In that case a homogeneous immobilization of ruthenium complexes, for example, takes place in PVC with low plasticizer concentrations. This material is then used as cladding for an optical waveguide and is optically excited by this waveguide. Suitable dyes include ruthenium, osmium and iridium complexes, the complexes being electrically saturated by means of a compensating ion. As polymers PVC, polyvinyl butyral, and polyvinyl acetate are used. Suitable plasticizers are the derivatives of phthalic acid, benzoic acid, sebacic acid, adipic acid, as well as paraffins. Typical solvents are acetone and ethanol. A typical sensor membrane described in EP 0 190 830 would thus consist of PVC, Ru(diph)$_3$ perchlorate as a dye, diisobutyl phthalate as a plasticizer, and dichloromethane as a solvent.

Known sensor membranes thus contain inorganic salts of transition metal complexes bonded to supporting materials, which are either contained as fillers in the polymer, or separately added to the polymer, or dissolved in the plasticizer component of a matrix. The polymers used in the above applications essentially are silicone rubbers curing at room temperature (Silicon RTV-118 of Wacker Chemie, Burghausen, Germany, or GE RTV SILASTIC 118 of General Electric, USA), or typical PVC materials.

SUMMARY OF THE INVENTION

It is an object of the invention to propose a sensor membrane containing the indicator substance, which should not be leached by the sample medium, in as homogeneous a distribution as possible, in addition to having a high sensitivity to the analytes cited above, while permitting easy reproducibility of such sensor membranes.

In the invention this object is achieved by providing that the polymer matrix essentially consist of at least one substance belonging to the group of cellulose derivatives, polystyrenes, polytetrahydrofuranes, or their respective derivatives, in which the indicator substance is provided in homogeneous distribution.

Unexpectedly it has been found that the transition metal complexes of the invention are highly soluble in the polymer materials mentioned and that neither supporting media nor plasticizers are required. In addition, the indicators are not leached by the sample medium, advantageously permitting very high indicator concentrations, which will result in very high signal intensities. The high signal intensity permits the use of extremely thin sensors characterized by an extremely quick response. Their oxygen sensitivity equals that of the sensor membranes known from the Mikrochimica Acta article referred to above.

In a variant of the invention the polymer matrix contains a mixture of ethyl cellulose and cellulose triacetate, or rather, the polymer matrix contains a mixture of polystyrene and polytetrahydrofuran.

Finally, the invention provides that the inorganic salt of the transition metal complex contain Ru, Os, Ir, Rh, Pd, Pt, or Re as a central atom, and 2,2'-bipyridine (bpy), 1,10-phenanthroline (phen), or 4,7-diphenyl-1,10-phenanthroline (diph) as a ligand, and $ClO_4$, Cl or $SO_4$ as a compensating ion.

Following are examples for the production of sensor membranes in accordance with the invention.

EXAMPLE 1

5 g ethyl cellulose are dissolved in 100 ml trichloromethane, and $5 \times 10^{-5}$ mol/l of the indicator dye $Ru(diph)_3(ClO_4)_2$ are added and dissolved by stirring. The solution is applied as a thin film on a mylar sheet by known techniques, such as spin coating or knife coating. The solvent is evaporated.

EXAMPLE 2

5 g cellulose triacetate are dissolved in 100 ml trichloromethane and $5 \times 10^{-4}$ mol/l of the indicator dye $Ru(diph)_3(ClO_4)_2$ are added; the mixture is dissolved by stirring. This solution is applied as a homogeneous film on mylar by known techniques, such as spin coating or knife coating, and the solvent is evaporated.

EXAMPLE 3

A mixture of equal parts of polystyrene and polytetrahydrofuran is dissolved in tetrahydrofuran, and $3 \times 10^{-5}$ mol/l of the indicator dye $Ru(diph)_3(ClO_4)_2$ are added and dissolved by stirring. The solution is applied on mylar at a film thickness of 3 micrometers by known techniques, such as spin coating or knife coating. The solvent is evaporated.

What is claimed is:

1. Method for preparing a sensor comprising:
   (a) providing a supporting surface;
   (b) providing a solution free of plasticizer comprising:
      (i) a polymer selected from the group consisting of polystyrene and polystyrene derivatives, and
      (ii) a salt of a transition metal complex having α-diimine ligands wherein said transition metal is selected from the group consisting of Ru, Os, Ir, Rh, Pd, Pt and Re;
   (c) applying said solution onto the supporting surface; and
   (d) evaporating solvent from said applied solution to form a sensor layer wherein the said salt of a transition metal complex is homogeneously distributed in said polymer.

2. Method according to claim 1 wherein said salt of a transition metal complex includes a ligand selected from the group consisting of 2,2'-bipyridine, 1,10-phenanthroline and 4,7-diphenyl-1,10-phenanthroline and an anion selected from the group consisting of $ClO_4$, Cl and $SO_4$.

* * * * *

UNITED STATES PATENT AND TRADEMARK OFFICE
CERTIFICATE OF CORRECTION

PATENT NO. : 6,139,798
DATED : October 31, 2000
INVENTOR(S) : Klimant et al.

It is certified that error appears in the above-identified patent and that said Letters Patent is hereby corrected as shown below:

<u>Title page,</u>
Item [57] ABSTRACT,
Line 5, "is," should read -- is --; and "indirectly," should read -- indirectly --
Line 12, "polytetrahydrofuranes" should read -- polytetrahydrofurans --

<u>Column 1,</u>
Line 17, "sample" should read -- sample, --
Line 19, "indirectly," should read -- indirectly --
Line 23, "ligands" should read -- ligands --
Line 28, "charge" should read -- change --
Line 40, "Ru(bpy)" should read -- Ru(bpy)$_3$ --
Line 41, "$_3$Cl$_2$." should read -- Cl$_2$. --

<u>Column 2,</u>
Line 37, "polytetrahydrofuranes" should read -- polytetrahydrofurans --

<u>Column 3,</u>
Line 8, "Ru(diph)" should read -- Ru(diph)$_3$ --
Line 9, "$_3$(ClO$_4$)$_2$" should read -- (ClO$_4$)$_2$ --

Signed and Sealed this

Second Day of April, 2002

*Attest:*

JAMES E. ROGAN
*Attesting Officer*     *Director of the United States Patent and Trademark Office*